(12) United States Patent
Geng

(10) Patent No.: US 11,442,499 B2
(45) Date of Patent: Sep. 13, 2022

(54) DISPLAY POSITION ADJUSTING METHOD, APPARATUS AND SYSTEM

(71) Applicant: BOE TECHNOLOGY GROUP CO., LTD., Beijing (CN)

(72) Inventor: Lihua Geng, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 538 days.

(21) Appl. No.: 16/466,609

(22) PCT Filed: Nov. 7, 2018

(86) PCT No.: PCT/CN2018/114287
§ 371 (c)(1),
(2) Date: Jun. 4, 2019

(87) PCT Pub. No.: WO2019/174280
PCT Pub. Date: Sep. 19, 2019

(65) Prior Publication Data
US 2020/0356135 A1    Nov. 12, 2020

(30) Foreign Application Priority Data
Mar. 13, 2018   (CN) .......................... 201810203586.X

(51) Int. Cl.
*G06F 1/16* (2006.01)
*H04N 13/366* (2018.01)
(Continued)

(52) U.S. Cl.
CPC ......... *G06F 1/1601* (2013.01); *F16M 11/046* (2013.01); *F16M 11/08* (2013.01);
(Continued)

(58) Field of Classification Search
CPC ........... G06F 1/1601; G06F 2200/1637; G06F 3/012; G06F 1/1607; G06F 1/163;
(Continued)

(56) References Cited

U.S. PATENT DOCUMENTS

| 4,111,184 A | * | 9/1978 | Fletcher | ................ | F24S 30/452 |
| | | | | | 136/246 |
| 4,509,501 A | * | 4/1985 | Hunter | .................... | F24S 23/79 |
| | | | | | 126/609 |

(Continued)

FOREIGN PATENT DOCUMENTS

| CN | 200980396 Y | 11/2007 |
| CN | 201420938 Y | 3/2010 |

(Continued)

OTHER PUBLICATIONS

International Search Report and Written Opinion of the International Searching Authority (with English language translation), International Application No. PCT/CN2018/114287, dated Feb. 19, 2019, 13 pp.

(Continued)

*Primary Examiner* — Douglas M Wilson
(74) *Attorney, Agent, or Firm* — Myers Bigel, P.A.

(57) ABSTRACT

A display position adjusting apparatus includes a processor and an arcuate bracket. The arcuate bracket includes a first arcuate rod and a second arcuate rod that are disposed perpendicular to each other. The display is disposed on the second arcuate rod. The display is connected to the second arcuate rod through the first connector and configured to move along the second arcuate rod through the first connector under a control of the processor. The second arcuate rod is connected to the first arcuate rod through a second (Continued)

connector, and configured to move along the first arcuate rod through the second connector under the control of the processor.

19 Claims, 4 Drawing Sheets

(51) Int. Cl.
| | | |
|---|---|---|
| *F16M 11/04* | (2006.01) | |
| *F16M 11/08* | (2006.01) | |
| *F16M 11/12* | (2006.01) | |
| *F16M 11/18* | (2006.01) | |
| *G05G 9/04* | (2006.01) | |
| *G06F 3/01* | (2006.01) | |
| *A61B 90/00* | (2016.01) | |

(52) U.S. Cl.
CPC ...... *H04N 13/366* (2018.05); *A61B 2090/372* (2016.02); *F16M 11/043* (2013.01); *F16M 11/045* (2013.01); *F16M 11/12* (2013.01); *F16M 11/126* (2013.01); *F16M 11/18* (2013.01); *G05G 9/04* (2013.01); *G06F 3/012* (2013.01); *G06F 2200/1637* (2013.01)

(58) Field of Classification Search
CPC ...... G06F 1/1694; G06F 1/1698; G06F 1/182; H04N 13/366; F16M 11/046; F16M 11/08; F16M 11/045; F16M 11/24; F16M 13/02; F16M 11/2021; F16M 11/18; F16M 11/06; F16M 11/12; F16M 11/126; F16M 11/043; A61B 2090/372; G05G 9/04

See application file for complete search history.

(56) References Cited

U.S. PATENT DOCUMENTS

| | | | |
|---|---|---|---|
| 2007/0120876 A1* | 5/2007 | Nishida | G09G 3/36 345/690 |
| 2013/0114146 A1* | 5/2013 | Larson | G02B 27/01 359/632 |
| 2014/0117174 A1 | 5/2014 | Tan et al. | |
| 2016/0274358 A1* | 9/2016 | Yajima | G02B 27/0093 |
| 2017/0111633 A1* | 4/2017 | Kang | H04N 13/317 |
| 2019/0118386 A1 | 4/2019 | Okumura et al. | |

FOREIGN PATENT DOCUMENTS

| | | |
|---|---|---|
| CN | 201964114 U | 9/2011 |
| CN | 202733363 U | 2/2013 |
| CN | 103047516 A | 4/2013 |
| CN | 203927298 U | 11/2014 |
| CN | 105049760 A | 11/2015 |
| CN | 205137005 U | 4/2016 |
| CN | 105933693 A | 9/2016 |
| CN | 206268738 U | 6/2017 |
| CN | 107105221 A | 8/2017 |
| CN | 108397654 A | 8/2018 |
| DE | 102012202957 A1 | 8/2013 |
| JP | 2017216643 A | 12/2017 |

OTHER PUBLICATIONS

First Office Action and English language translation, CN Application No. 201810203586.X, dated Feb. 25, 2019, 19 pp.

* cited by examiner

DISPLAY POSITION ADJUSTING METHOD, APPARATUS AND SYSTEM

CROSS REFERENCE TO RELATED APPLICATIONS

The present application is a 35 U.S.C. 371 national stage application of PCT International Application No. PCT/CN2018/114287, filed on Nov. 7, 2018, which claims the benefit of Chinese Patent Application No. 201810203586.X, filed on Mar. 13, 2018, the contents of which are incorporated herein by reference in their entireties.

FIELD

The present disclosure relates to display technologies, and specifically to a display position adjusting method, apparatus and system.

BACKGROUND

Due to technical limitations, an effective viewing angle of most displays is relatively small (i.e., the viewing angle is small). When viewing the display, a viewing implementor of the display must view within a specific distance and effective viewing angle. Only when the line of sight of the viewing implementor of the display falls on a central position of the display and is perpendicular to the display surface, a better viewing effect can be obtained, otherwise the viewing effect is undesirable.

For example, during endoscopic surgery, the surgeon can perform surgery in real time by viewing the internal tissue of the human body imaged on a medical display, whereupon high viewing quality and effect is needed.

A viewing implementor of the display who needs to watch the display for a long time and needs to obtain a better viewing effect is prone to fatigue of the body especially the neck. For example, a surgeon who uses the display for endoscopic surgery needs to stare at the display for a long time, his head needs to maintain a posture for a long time, and the neck is under great pressure. When the head is turned up and down or left and right to change a posture, it is very easy to cause the viewing effect to deteriorate.

At present, for the case in which the viewing implementor of the display changes a viewing angle, it is difficult to achieve a better viewing effect by adjusting the position of the display.

SUMMARY

The present disclosure provides a display position adjusting method, apparatus and system to achieve a better viewing effect by adjusting the position of the display.

In a first aspect, an exemplary embodiment of the present disclosure provides a display position adjusting apparatus, comprising a processor and an arcuate bracket, wherein:
the arcuate bracket comprises a first arcuate rod and a second arcuate rod disposed perpendicular to each other, and the display is disposed on the second arcuate rod;
the display is connected to the second arcuate rod through a first connector, and configured to move along the second arcuate rod through the first connector under the control of the processor; and
the second arcuate rod is connected to the first arcuate rod through a second connector and configured to move along the first arcuate rod through the second connector under the control of the processor.

According to an aspect of the disclosure, the display position adjusting apparatus may further comprise:
a height sensor disposed on the arcuate bracket and used to measure a height of the arcuate bracket;
a support rod for supporting the arcuate bracket, the first arcuate rod being connected to the support rod through a third connector, and configured to move along the support rod through the third connector under the control of the processor according to height data of the height sensor.

According to an aspect of the disclosure, each of the first connector, the second connector and the third connector comprises a motor and a gear, wherein the motor drives the gear to rotate under the control of the processor, so that the first connector, the second connector and the third connector move along the corresponding second arcuate rod, the first arcuate rod or the support rod.

Optionally, the processor is configured to:
obtain angle change data of a viewing implementor of the display; and
adjust the position of the display on the arcuate bracket according to the angle change data of the viewing implementor of the display until a plane of the display is perpendicular to the line of sight of the viewing implementor of the display.

In a second aspect, an exemplary embodiment of the present disclosure further provides a display position adjusting method using the apparatus as described in the first aspect, comprising the steps of:
obtaining angle change data of a viewing implementor of the display is through the processor; and
adjusting the position of the display on the arcuate bracket according to the angle change data of the viewing implementor of the display until a plane of the display is perpendicular to the line of sight of the viewing implementor of the display.

According to an aspect of the present disclosure, the angle change data comprises a vertical angle change value and a horizontal angle change value, the first arcuate rod is vertically disposed, and the second arcuate rod is horizontally disposed, wherein the adjusting the position of the display on the arcuate bracket according to the angle change data of the viewing implementor of the display until the display plane is perpendicular to the line of sight of the viewing implementor of the display specifically comprises:
moving the second arcuate rod on the first arcuate rod by an arc length corresponding to the vertical angle change value, and moving the display on the second arcuate rod by an arc length corresponding to the horizontal angle change value.

Alternatively, the angle change data comprises a vertical angle change value and a horizontal angle change value, the first arcuate rod is horizontally disposed, and the second arcuate rod is vertically disposed, wherein the adjusting the position of the display on the arcuate bracket according to the angle change data of the viewing implementor of the display until the display plane is perpendicular to the line of sight of the viewing implementor of the display comprises:
moving the display on the second arcuate rod by an arc length corresponding to the vertical angle change value, and moving the second arcuate rod on the first arcuate rod by an arc length corresponding to the horizontal angle change value.

According to an aspect of the disclosure, before the obtaining the angle change data of the viewing implementor of the display, the method further comprises:

adjusting the position of the arcuate bracket according to the position of the viewing implementor of the display such that the viewing implementor of the display is located at a sphere center of the arcuate bracket.

According to an aspect of the present disclosure, the adjusting the position of the arcuate bracket according to the position of the viewing implementor of the display such that the viewing implementor of the display is located at a sphere center of the arcuate bracket comprises:

adjusting the height of the arcuate bracket to be consistent with the height of the viewing implementor of the display according to height data of an observation point of the viewing implementor of the display and height data determined by the height sensor on the arcuate bracket; and according to distance data of the viewing implementor of the display and the arcuate bracket, adjusting the distance between the arcuate bracket and the viewing implementor of the display to be consistent with a radius of the arcuate bracket.

According to an aspect of the disclosure, the arcuate bracket is disposed on a support rod, and the support rod is disposed on a base. Adjusting the height of the arcuate bracket to be consistent with the height of the observation point of the viewing implementor of the display comprises: adjusting the position of the arcuate bracket on the support rod until the height of the arcuate bracket is consistent with the height of the observation point of the viewing implementor of the display. Adjusting the distance between the arcuate bracket and the viewing implementor of the display to be consistent with the radius of the arcuate bracket comprises: moving the base until the distance between the arcuate bracket and the viewing implementor of the display is consistent with the radius of the arcuate bracket.

In a third aspect, an exemplary embodiment of the present disclosure further provides a 3D display position adjusting system, comprising:

a 3D viewing device configured to transmit the angle change data when its viewing angle changes; and a 3D display position adjusting apparatus, the apparatus comprising a processor and an arcuate bracket, wherein: the arcuate bracket comprises a first arcuate rod and a second arcuate rod disposed perpendicularly to each other, and the 3D display is disposed on the second arcuate rod; the 3D display is connected to the second arcuate rod through a first connector, and configured to move along the second arcuate rod through the first connector under the control of the processor; the second arcuate rod is connected to the first arcuate rod through a second connector and configured to move along the first arcuate rod through the second connector under the control of the processor; the 3D display position adjusting apparatus is configured to obtain the angle change data of the 3D viewing device, and adjust the position of the 3D display on the arcuate bracket according to the angle change data of the 3D viewing device until the 3D display plane is perpendicular to the line of sight of the user of the 3D viewing device.

Optionally, the angle change data comprises a vertical angle change value and a horizontal angle change value, the first arcuate rod is vertically disposed, and the second arcuate rod is horizontally disposed, wherein adjusting, by the 3D display position adjusting apparatus, the position of the 3D display on the arcuate bracket according to the angle change data of the 3D viewing device until the 3D display plane is perpendicular to the line of sight of the 3D viewing device, comprises:

moving the second arcuate rod on the first arcuate rod by an arc length corresponding to the vertical angle change value, and moving the 3D display on the second arcuate rod by an arc length corresponding to the horizontal angle change value.

Alternatively, the angle change data comprises a vertical angle change value and a horizontal angle change value, the first arcuate rod is horizontally disposed, the second arcuate rod is vertically disposed, wherein adjusting, by the 3D display position adjusting apparatus, the position of the 3D display on the arcuate bracket according to the angle change data of the 3D viewing device until the 3D display plane is perpendicular to the line of sight of the user of the 3D viewing device, specifically comprises:

moving the 3D display on the second arcuate rod by an arc length corresponding to the vertical angle change value, and moving the second arcuate rod on the first arcuate rod by an arc length corresponding to the horizontal angle change value.

According to one aspect of the present disclosure, the 3D display position adjusting apparatus is further configured to:

before obtaining the angle change data of the 3D viewing device, adjust the position of the arcuate bracket according to the position of the user so that the 3D viewing device is located at a sphere center of the arcuate bracket.

According to an aspect of the present disclosure, the 3D viewing device is configured to obtain height data of the 3D viewing device and distance data of the 3D viewing device and the arcuate bracket, and transmit the height data and distance data to the 3D display position adjusting apparatus, wherein the adjusting, by the 3D display position adjusting apparatus, the position of the arcuate bracket according to the position of the user, so that the 3D viewing device is located at the sphere center of the arcuate bracket, specifically comprises:

adjusting the height of the arcuate bracket to be consistent with the height of the 3D viewing device according to height data of the 3D viewing device and height data determined by the height sensor on the arcuate bracket; and according to distance data of the 3D viewing device and the arcuate bracket, adjusting the distance between the arcuate bracket and the 3D viewing device to be consistent with a radius of the arcuate bracket.

According to an aspect of the present disclosure, the arcuate bracket is disposed on a support rod, and the support rod is disposed on a base; wherein the adjusting, by the 3D display position adjusting apparatus, the height of the arcuate bracket to be consistent with the height of the viewing implementor of the 3D display comprises: adjusting the position of the arcuate bracket on the support rod until the height of the arcuate bracket is consistent with the height of the viewing implementor of the 3D display; wherein the adjusting, by the 3D display position adjusting apparatus, the distance between the arcuate bracket and the viewing implementor of the 3D display to be consistent with a radius of the arcuate bracket comprises: moving the base until the distance between the arcuate bracket and the viewing implementor of the 3D display is consistent with the radius of the arcuate bracket.

BRIEF DESCRIPTION OF DRAWINGS

Other features, objects, and advantages of the present application will become more apparent from the detailed description of unrestrictive embodiments with reference to figures.

DETAILED DESCRIPTION

Figure 1:
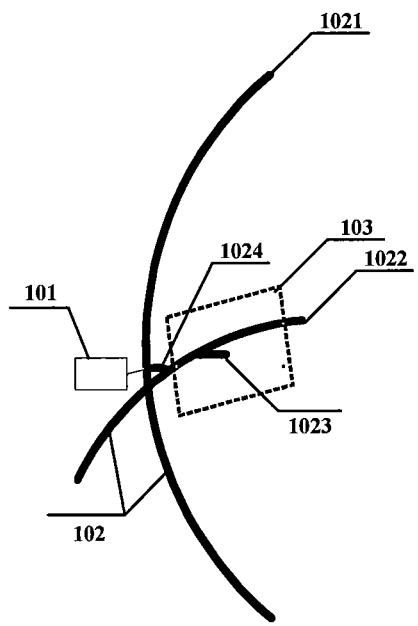
FIG. 1 is a schematic structural diagram of a 3D display position adjusting apparatus according to an exemplary embodiment of the present disclosure.

The present application will be further described in detail below with reference to the figures and embodiments. It may be appreciated that specific embodiments described herein are merely used to illustrate the present disclosure and are not intended to limit the present disclosure. It should also be noted that, for the convenience of description, only parts related to the disclosure are shown in the figures.

It needs to be appreciated that the embodiments in the present application and the features in the embodiments may be combined with one another in the absence of confliction. The present application will be described in detail below with reference to the figures.

Since a 3D display imposes more rigorous requirements for the viewing angle and the viewing distance, the display position adjusting method, apparatus and system according to the present disclosure are particularly adapted for the 3D display. Therefore, the display position adjusting method, apparatus and system of the present disclosure will be illustrated by taking the 3D display as an example. However, it should be emphasized that although the present disclosure will be described in detail below by taking the 3D display as an example, it should be understood that the described 3D display position adjusting method, apparatus and system are also applicable to non-3D displays.

The 3D display is also called a stereo display or 3D polarized display. Two major 3D display technology systems have been developed which require and do not require the wearing of 3D glasses (or polarized glasses). Currently, conventional 3D displays require viewers to wear polarized glasses to view to create a three-dimensional effect. The display technology that does not require the wearing of the 3D glasses, namely, naked eye 3D display technology is the most advanced high-technology in the imaging industry. The 3D displays described herein include 3D displays that require and do not require the wearing of 3D glasses.

Definition of Terms

A viewer of the 3D display (or a user of the 3D display): the term refers to a person viewing the 3D display, and is hereinafter referred to as a viewer (or user).

3D viewing device: the term refers to a device worn by the viewer of the 3D display to view the 3D display, and for example includes, but not limited to, at least one of the following: 3D glasses, an angle sensor, an angle data transmitter, a distance sensor, a height sensor, a three-axis gyroscope, a processor, a wireless transmitter module, a battery and a circuit.

A viewing implementor of the 3D display: it may refer to a viewer of the 3D display, or may refer to a 3D viewing device, or may also refer to both the viewer of the 3D display and the 3D viewing device. That is, it covers the viewer of the 3D display and/or the 3D viewing device. The term is hereinafter referred to as the viewing implementor or implementor.

Arcuate: "arcuate" herein refers to a circular arc shape.

A spherical surface of an arcuate bracket: refers to a spherical profile surface of the entire arcuate bracket.

A sphere center of the spherical surface of the arcuate bracket: the term is also referred to as a sphere center of the arcuate bracket, and refers to the sphere center of the spherical profile surface of the entire arcuate bracket.

A center of the arcuate bracket: it refers to a geometrical center of the arcuate bracket and is located on the geometry of the arcuate bracket.

A plane where an arcuate rod lies: it refers to a common surface of the arcuate rod and its chord.

Referring to FIG. 1, the 3D display position adjusting apparatus provided by an exemplary embodiment of the present disclosure includes a processor 101 and an arcuate bracket 102, wherein:

the arcuate bracket 102 includes a first arcuate rod 1021 and a second arcuate rod 1022 disposed perpendicularly to each other, and a 3D display 103 is disposed on the second arcuate rod 1022;

the 3D display 103 is connected to the second arcuate rod 1022 through a first connector 1023, and configured to move along the second arcuate rod 1022 through the first connector 1023 under the control of the processor 101; and the second arcuate rod 1022 is connected to the first arcuate rod 1021 through a second connector 1024, and configured to move along the first arcuate rod 1021 through the second connector 1024 under the control of the processor 101.

With the 3D display position adjusting apparatus, the 3D display may move on the arcuate bracket. When the viewing angle of the viewing implementor of the 3D display changes, it is possible to keep the 3D display perpendicular to the line of sight of the viewing implementor of the 3D display through the movement of the 3D display on the arcuate bracket, and thereby enable the viewing implementor of the 3D display to achieve a better 3D viewing effect.

As for an application scenario in which the viewing implementor of the 3D display needs to change the viewing angle and position and has a higher requirement for the displaying effect, it is possible to, through the 3D display position adjusting apparatus, keep the distance and viewing angle between the viewing implementor of the 3D display consistent and thereby obtain a better viewing effect, and possible to automatically adjust the orientation of the 3D display according to the movement of the viewer's head to maintain the better viewing distance and viewing angle.

Figure 2:
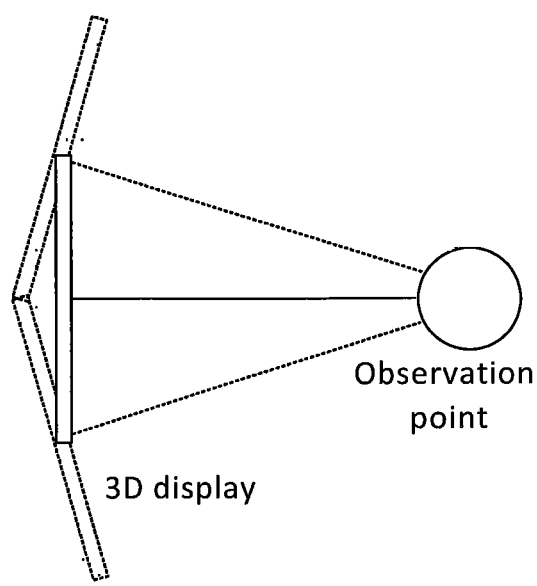
FIG. 2 is a schematic view of a preferred viewing angle in a vertical direction according to an exemplary embodiment of the present disclosure.
Figure 3:
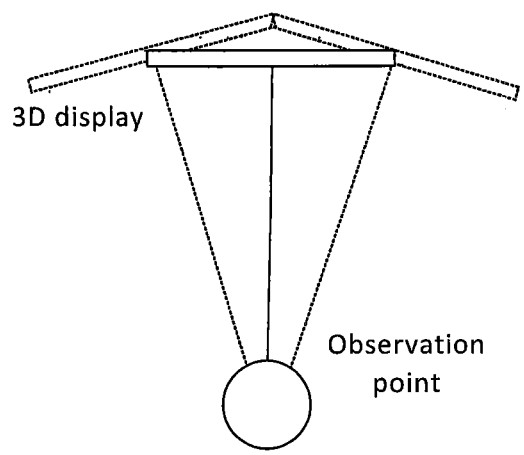
FIG. 3 is a schematic diagram of a preferred viewing angle in a horizontal direction according to an exemplary embodiment of the present disclosure.

When a viewing point of the viewing implementor of the 3D display is located at a position of the sphere center of the arcuate bracket, as long as the 3D display makes a spherical motion following the viewer's line of sight along the arcuate bracket, real-time optimal matching of the distance and viewing angle between the viewer and the screen of the 3D display can be achieved (the viewing distance is R, and the line of sight is perpendicular to the plane of the 3D display), as shown in FIG. 2 and FIG. 3. FIG. 2 shows a preferred viewing angle in a vertical direction, and FIG. 3 shows a preferred viewing angle in a horizontal direction.

Free movement of the 3D display on the spherical surface of the arcuate bracket may be achieved through the 3D display position adjusting apparatus provided by the exemplary embodiment of the present disclosure; as long as the viewing point of the viewing implementor of the 3D display is located at the position of the spherical center of the spherical surface, no matter how the viewer's head moves, the bracket may keep the distance and viewing angle between the viewing implementor of the 3D display and the 3D display unchanged by adjusting the position of the display on the spherical surface, thereby maintaining a better viewing effect.

In use, the arcuate bracket may be fixed on a wall surface, a fixing position needs to match the position of the viewing implementor of the 3D display, and the viewing implementor of the 3D display needs to be located at the center of the arcuate bracket. For example, eyes (i.e., an observing point or viewing point) of the viewer of the 3D display need to be located at the spherical center of the arcuate bracket; or the observing point or viewing point of the 3D viewing device (e.g., 3D glasses) is located at the spherical center of the arcuate bracket.

Furthermore, in order to enable the apparatus to better meet demands of viewing implementors of a plurality of different 3D displays or of use scenarios, the apparatus may further include a support rod 105 for supporting the arcuate bracket 102, and the arcuate bracket 102 is movable vertically on the support rod, thereby adjusting the height of the arcuate bracket.

In order to facilitate adjusting the height of the arcuate bracket 102, the apparatus may further include a height sensor disposed on the arcuate bracket 102 and used to measure the height of the arcuate bracket 102, so as to adjust the height of the arcuate bracket 102 according to the data of the height sensor.

Figure 4:
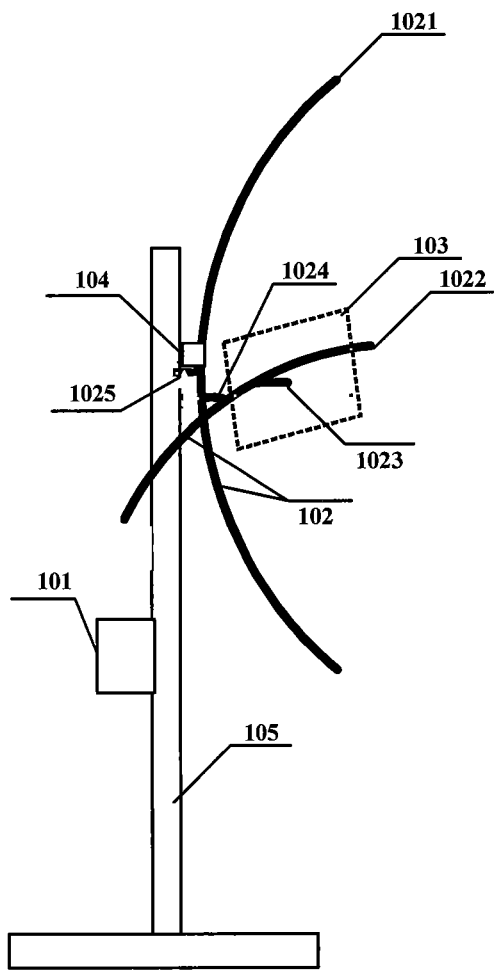
FIG. 4 is a schematic structural diagram of an optional 3D display position adjusting apparatus according to an exemplary embodiment of the present disclosure.

Specifically, as shown in FIG. 4, the 3D display position adjusting apparatus provided by the exemplary embodiment of the present disclosure may include: a height sensor 104 disposed on the arcuate bracket 102 and used to measure the height of the arcuate bracket 102; and a support rod 105 for supporting the arcuate bracket, wherein the first arcuate rod 1021 is connected to the support rod 105 through a third connector 1025, and configured to move along the support rod 105 through the third connector 1025 under control of the processor 101 according to the height data of the height sensor.

The height sensor 104 may determine a distance from the ground by means of laser sensing, infrared sensing or ultrasonic sensing. When the height adjustment of the arcuate bracket is performed according to the height of the central position of the arcuate bracket, if the height sensor 104 is disposed at the central position of the arcuate bracket, the height of the central position of the arcuate bracket may be conveniently obtained; if the height sensor is disposed at other positions of the arcuate bracket, a height conversion is required to determine the height of the central position of the arcuate bracket.

Through the height sensor 104 and the support rod 105, the height of the arcuate bracket 102 may be adjusted relatively easily. Furthermore, the support rod 105 may be disposed on the base, and the base is movable to facilitate adjustment of the distance between the arcuate bracket 102 and the 3D display. Through the adjustment of the height and distance, it is relatively easy to assist the user in realizing coincidence of the spherical center of the spherical support 102 and the viewing point of the viewing implementor of the 3D display.

Specifically, the base may be a circular or rectangular base, and a bottom of the base may further be mounted with a roller to facilitate the free movement of the base. The support rod 105 may be a cylindrical straight rod acting to support and disposed perpendicular to the base.

The first arcuate rod 1021 and the second arcuate rod 1022 are respectively one-third of the arc length of an entire circular shape they correspond to, or may be adjusted according to actual situations. The larger the spherical surface formed by the first arcuate rod 1021 and the second arcuate rod 1022 is, the larger the adjustable range is. Conversely, the smaller the spherical surface formed by the first arcuate rod 1021 and the second arcuate rod 1022 is, the smaller the adjustable range is. The radius of the spherical shape is in a direction proportional relationship with the height H of the 3D display. The radii of the circles corresponding to the first arcuate rod 1021 and the second arcuate rod 1022 are the same.

Figure 5:
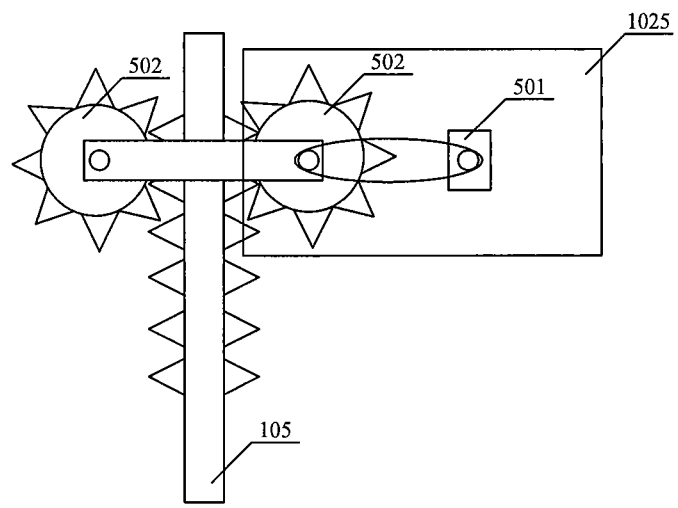
FIG. 5 is a schematic structural diagram of a third connector according to an exemplary embodiment of the present disclosure.

As shown in FIG. 5, in the apparatus provided by the exemplary embodiment of the present disclosure, the first connector 1023, the second connector 1024 and the third connector 1025 each include a motor 501 and a gear 502. The motor 501 drives the gear 502 to rotate under the control of the processor 101, so that the first connector 1023, the second connector 1024 and the third connector 1025 move along the corresponding second arcuate rod 1022, the first arcuate rod 1021 or the support rod 105.

Detailed illustration will be presented below by taking the viewing implementor of the 3D display as the 3D viewing device.

Figure 6:
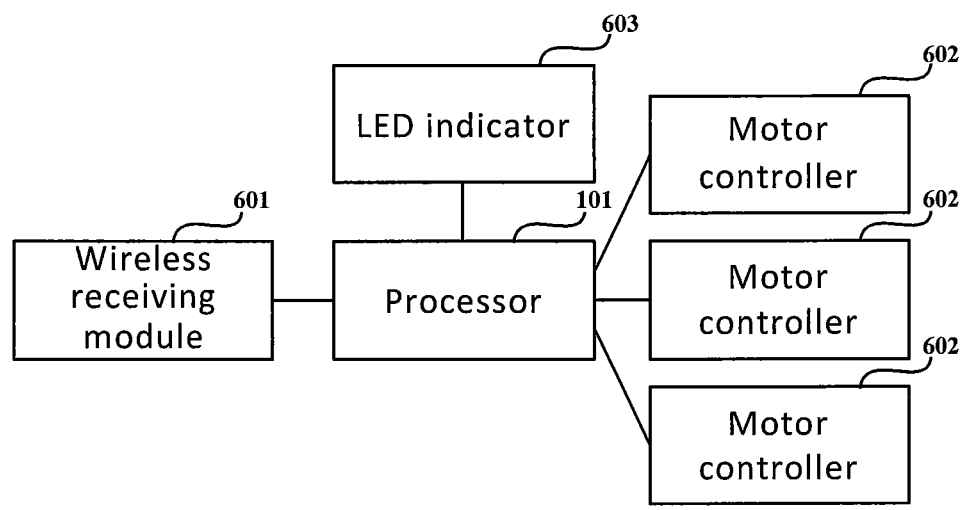
FIG. 6 is a schematic diagram of connection of a circuit of a processor in a 3D display position adjusting apparatus according to an exemplary embodiment of the present disclosure.

The processor 101 may respectively control motors in respective connectors to operate through motor controllers, and drive the corresponding gears to rotate. The circuit connection relationship of the processor 101 is as shown in FIG. 6, wherein there is included a wireless receiving module 601 for receiving content sent by a wireless transmitting module in a 3D viewing device of the viewing implementor of the 3D display. The processor 101 is used to perform data processing and control of the motor controllers. The motor controllers 602 may generate different driving currents according to different control information of a microcontroller, to drive the corresponding motor to rotate in a prescribed direction and angle. Furthermore, the processor 101 may also be connected to an LED indicator 603. The LED indicator 603 includes one red LED lamp, one yellow LED lamp and one green LED lamp, and under the control of the processor 101, indicates whether the distance between the display and the user is appropriate and matched.

The processor 101, the motor controllers corresponding to respective motors, the wireless receiving module for receiving data transmitted by the 3D viewing device and the like may be collectively disposed, for example, may be collectively disposed in a control box and fixed on the support rod, or fixed in at an appropriate position of the arcuate bracket.

The processor 101 is specifically configured to:
- obtain angle change data of the 3D viewing device; and
- according to the angle change data of the 3D viewing device, adjust the position of the 3D display on the arcuate bracket until the 3D display plane is perpendicular to the line of sight of the viewing implementor of the 3D display.

Figure 7:
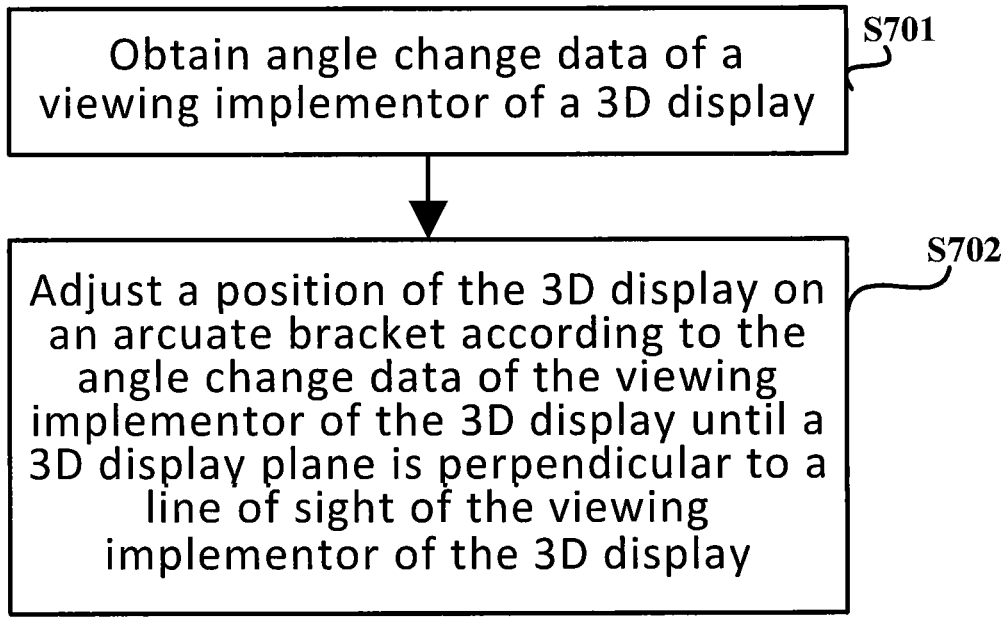
FIG. 7 is a flowchart of a 3D display position adjusting method according to an exemplary embodiment of the present disclosure.

As shown in FIG. 7, an exemplary embodiment of the present disclosure further provides a 3D display position adjustment method using the apparatus shown in FIG. 1, the method comprising:
- step S701: the processor obtains angle change data of the viewing implementor (for example, a 3D viewing device) of the 3D display; and
- step S702: adjusting the position of the 3D display on the arcuate bracket according to the angle change data of the viewing implementor of the 3D display until the 3D display plane is perpendicular to the line of sight of the viewing implementor of the 3D display.

Since the 3D display plane and the line of sight of the viewing implementor of the 3D display may maintain a perpendicular relationship by adjusting the position of the 3D display, the user may always obtain a better viewing experience, the requirement for the body position is lowered, and the viewing experience of the user is improved.

Specifically, when the first arcuate rod and the second arcuate rod are respectively located in the horizontal and vertical directions, it is convenient to calculate and adjust, and the amount of calculation may be reduced to a large extent. At this time, the angle change data in step S701 includes vertical angle change values and horizontal angle change values.

When the first arcuate rod is vertically disposed and the second arcuate rod is horizontally disposed, in step S702, the adjusting the position of the 3D display on the arcuate bracket according to the angle change data of the viewing implementor of the 3D display until the 3D display plane is perpendicular to the line of sight of the viewing implementor of the 3D display specifically includes: moving the second arcuate rod on the first arcuate rod by an arc length corresponding to the vertical angle change value, and moving the 3D display on the second arcuate rod by an arc length corresponding to the horizontal angle change value.

When the first arcuate rod is horizontally disposed and the second arcuate rod is vertically disposed, in step S702, the adjusting the position of the 3D display on the arcuate bracket according to the angle change data of the viewing implementor of the 3D display until the 3D display plane is perpendicular to the line of sight of the viewing implementor of the 3D display specifically includes: moving the 3D display on the second arcuate rod by an arc length corresponding to the vertical angle change value, and moving the second arcuate rod on the first arcuate rod by an arc length corresponding to the horizontal angle change value.

Before the viewing implementor of the 3D display starts to view, generally to ensure the viewing effect, an initial position of the arcuate bracket needs to be adjusted, so that the user's eyes and the worn 3D viewing device (the viewing point of the viewing implementor of the 3D display) are located in the spherical center of the arcuate bracket. If the position of the user is relatively fixed each time, the initial position adjustment may not be performed.

When the initial position adjustment is needed, before step S701, the method further includes adjusting the position of the arcuate bracket according to the position of the viewing implementor of the 3D display such that the viewing implementor of the 3D display is located at the spherical center of the arcuate bracket.

Specifically, performing position adjustment mainly lies in adjusting the height of the arcuate bracket and the distance between the arcuate bracket and the user. It may be seen that the adjusting the position of the arcuate bracket according to the position of user such that the viewing implementor of the 3D display is located at the spherical center of the arcuate bracket specifically includes:
- adjusting the height of the arcuate bracket to be consistent with the height of the viewing implementor of the 3D display according to the height data of the viewing implementor of the 3D display and the height data determined by the height sensor on the arcuate bracket; and
- according to the distance data of the viewing implementor of the 3D display and the arcuate bracket, adjusting the distance between the arcuate bracket and the viewing implementor of the 3D display to be consistent with the radius of the arcuate bracket.

When the arcuate bracket is disposed on the support rod and the support rod is disposed on the base, the adjusting the height of the arcuate bracket to be consistent with the height of the viewing implementor of the 3D display includes:
- adjusting the position of the arcuate bracket on the support rod until the height of the arcuate bracket is consistent with the height of the viewing implementor of the 3D display.

Adjusting the distance between the arcuate bracket and the viewing implementor of the 3D display to be consistent with the radius of the arcuate bracket includes:
- moving the base until the distance between the arcuate bracket and the viewing implementor of the 3D display is consistent with the radius of the arcuate bracket.

The step of moving the base may be performed under the control of the processor, or may be manually performed.

It should be noted that although operations of the method of the present disclosure are described in a particular order in the figures, this does not require or imply that these operations must be performed in the particular order, or that all of the operations shown must be performed to achieve the desired results. Instead, the steps depicted in the flowchart may be performed in a different order. Additionally or alternatively, certain steps may be omitted, multiple steps may be combined into one step for execution, and/or one step may be divided into multiple steps for execution.

The specific operation steps in the use are described in detail below:

In the scenario where the viewing implementor of the 3D display needs to change the orientation and has high requirements for the 3D viewing quality, the 3D display position adjusting apparatus and method provided by the exemplary embodiments of the present disclosure are used to first perform initial position adjustment to correct the initial height of the 3D display and the distance between the display and the viewing implementor of the 3D display, implement coincidence of the spherical center of the spherical surface defined by the profile of the arcuate bracket and the viewing point of the viewing implementor of the 3D display (i.e., the viewing distance is the radius R of the spherical surface, the viewing line falls on the center of the screen and remains perpendicular to the screen), and ensure a better initial viewing effect. Subsequent adjustment of the 3D display based on the position of the spherical surface is performed on this basis so that the effect after adjustment remains consistent with the initial effect.

After power on, an initial process is first performed (in the initial process, the 3D display will be adjusted to an initial position, that is, the first connector, the second connector and the third connector are on a straight line, and the plane where the display lies is perpendicular to the plane where the first arcuate rod and second arcuate rod lie). The initial process is divided into a height matching process and a distance matching process. The height matching is performed first, and then the distance matching is performed. Detailed illustration will be presented below by taking the viewing implementor of the 3D display as the 3D viewing device.

Height Matching

After the user wears the 3D viewing device, the height sensor on the 3D viewing device measures a height h1 of the 3D viewing device from the ground, and sends the height h1 to the 3D display position adjusting apparatus. The height sensor on the arcuate bracket may also collect a distance h2 between the central position of the arcuate bracket and the ground. The processor compares the heights h1 and h2, and drives the motor in the third connector to rotate through the motor controller to drive the first arcuate rod to move up and down along the support rod. When h1 is greater than h2, the first arcuate rod moves upwards. When h1 is smaller than h2, the first arcuate rod moves downward. During the adjustment process, the height sensor may continue to collect the height h2 in real time. When h1 and h2 are equal, the height matching process ends, and the central position of the bracket and the 3D viewing device are at the same vertical height.

Distance Matching

After the user wears the 3D viewing device, he stands at a fixed position and casts the line of sight to the 3D display. At this time, the distance sensor on the 3D viewing device starts working, to measure a distance L1 between the 3D viewing device and the 3D display, the 3D viewing device sends the L1 value to the 3D display position adjusting apparatus, and the apparatus compares L1 with a preset spherical radius L2. When L1 is greater than L2, a yellow lamp turns on, and prompts the user to push the bracket toward the 3D viewing device wearer. When L1 is smaller than L2, a red lamp turns on, and prompts the user to push the bracket away from the 3D viewing device wearer. The distance sensor on the 3D viewing device may work all the time, and transmit the distance information L1 to the 3D display position adjusting apparatus. When L1 and L2 are equal in the distance adjustment process, a green lamp turns on, indicating that the distance is appropriate, whereby the distance matching process ends.

Position Adjustment During Viewing

When the initial process is completed, the viewing may be performed. During the viewing process, when the head of the 3D viewing device wearer turns, a gyroscope in the 3D viewing device detects a turning direction and angle of the head. Assuming the head turns right by a rh angle in the horizontal direction and turn upward by a rv angle in the vertical direction, the 3D viewing device will send rh and rv to the 3D display position adjusting apparatus; the 3D display position adjusting apparatus drives the motor in the second connector through the corresponding motor controller, to drive the second arcuate rod to turn up by the rv angle along the first arcuate rod. Since the 3D display moves upward along the first arcuate rod, the distance between the display and the observation point is always maintained as L2(=R) during the movement. After the movement is completed, the angle in the vertical direction is matched with the user's line of sight; then, the motor in the first connector is driven by the corresponding motor controller to drive the 3D display to turn right by the rh angle along the second arcuate rod. Likewise, since the 3D display moves horizontally along the second arcuate rod, and the radii of the circles corresponding to the first arcuate rod 1021 and the second arcuate rod 1022 are the same, during the movement process the distance between the display and the observation point also remains unchanged L2 (=R). After the adjustment, the angle in the horizontal direction is matched with the user's line of sight. After the above adjustment, the user's line of sight still falls at the central position of the 3D display and is perpendicular to the 3D display plane, and the distance between the 3D viewing device and the 3D display remains at L2 (=R), thereby maintaining a better viewing effect.

Figure 8:
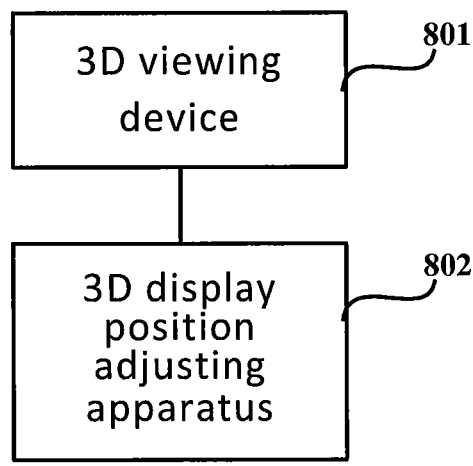
FIG. 8 is a schematic structural diagram of a 3D display position adjustment system according to an exemplary embodiment of the present disclosure.

Exemplary embodiments of the present disclosure further provide a 3D display position adjustment system. Illustration will be presented below by taking the viewing implementor of the 3D display as the 3D viewing device. As shown in FIG. 8, the 3D display position adjustment system includes:

a 3D viewing device 801 configured to transmit the angle change data when its viewing angle changes; and a 3D display position adjusting apparatus 802, the apparatus comprising a processor and an arcuate bracket, wherein: the arcuate bracket comprises a first arcuate rod and a second arcuate rod disposed perpendicularly to each other, and the 3D display is disposed on the second arcuate rod; the 3D display is connected to the second arcuate rod through a first connector, and configured to move along the second arcuate rod through the first connector under the control of the processor; the second arcuate rod is connected to the first arcuate rod through a second connector and configured to move along the first arcuate rod through the second connector under the control of the processor; the 3D display position adjusting apparatus is configured to obtain the angle change data of the 3D viewing device; and adjust the position of the 3D display on the arcuate bracket according to the angle change data of the 3D viewing device until the 3D display plane is perpendicular to the line of sight of the user of the 3D viewing device.

According to one aspect of the disclosure, the angle change data includes a vertical angle change value and a horizontal angle change value.

When the first arcuate rod is vertically disposed, the second arcuate rod is horizontally disposed, and the adjusting, by the 3D display position adjusting apparatus 802, the position of the 3D display on the arcuate bracket according to the angle change data of the 3D viewing device until the 3D display plane is perpendicular to the line of sight of the 3D viewing device specifically includes moving the second arcuate rod on the first arcuate rod by an arc length corresponding to the vertical angle change value, and moving the 3D display on the second arcuate rod by an arc length corresponding to the horizontal angle change value.

When the first arcuate rod is horizontally disposed, the second arcuate rod is vertically disposed, and the adjusting, by the 3D display position adjusting apparatus, the position of the 3D display on the arcuate bracket according to the angle change data of the 3D viewing device until the 3D display plane is perpendicular to the line of sight of the user of the 3D viewing device specifically includes moving the 3D display on the second arcuate rod by an arc length corresponding to the vertical angle change value, and moving the second arcuate rod on the first arcuate rod by an arc length corresponding to the horizontal angle change value.

According to one aspect of the present disclosure, the 3D display position adjusting apparatus 802 is further configured to:

before obtaining the angle change data of the 3D viewing device, adjust the position of the arcuate bracket according to the position of the user so that the 3D viewing device is located at the spherical center of the arcuate bracket.

The 3D viewing device 801 is configured to obtain height data of the 3D viewing device and distance data of the 3D viewing device and the arcuate bracket, and transmit the height data and distance data to the 3D display position adjusting apparatus.

Adjusting, by the 3D display position adjusting apparatus 802, the position of the arcuate bracket according to the position of the 3D viewing device, so that the 3D viewing device is located at the spherical center of the arcuate bracket specifically includes:

adjusting the height of the arcuate bracket to be consistent with the height of the 3D viewing device according to the height data of the 3D viewing device and the height data determined by the height sensor on the arcuate bracket; and according to the distance data of the 3D viewing device 801 and the arcuate bracket, adjusting the distance between the arcuate bracket and the 3D viewing device 801 to be consistent with a radius of the arcuate bracket.

According to an aspect of the present disclosure, the arcuate bracket is disposed on the support rod, and the support rod is disposed on the base.

The adjusting, by the 3D display position adjusting apparatus 802, the height of the arcuate bracket to be consistent with the height of the 3D viewing device 801 specifically includes: adjusting the position of the arcuate bracket on the support rod until the height of the arcuate bracket is consistent with the height of the 3D viewing device 801.

The adjusting, by the 3D display position adjusting apparatus 802, the distance between the arcuate bracket and the 3D viewing device 801 to be consistent with a radius of the arcuate bracket specifically includes: moving the base until the distance between the arcuate bracket and the 3D viewing device 801 is consistent with the radius of the arcuate bracket.

A common form of the 3D viewing device 801 is 3D glasses with a function. The 3D viewing device may include: a distance sensor, a height sensor, a three-axis gyroscope, a processor, a wireless transmitting module, a button battery, and a circuit and a battery. The circuit and the battery may be respectively mounted on either side of the glasses. No limitation is imposed on which one of the circuit and the battery is mounted on the left side or right side of the 3D viewing device. The circuit includes a distance sensor, a height sensor, a three-axis gyroscope, a processor and a wireless transmitting module. The distance sensor faces forward, parallel to the wearer's line of sight, and may measure the distance between the glasses and an obstacle in the front; the height sensor faces downward, pointes to the ground, and may measure the distance between the glasses and the ground; the three-axis gyroscope is mounted inside the circuit board, and may measure the turning angle of the wearer's head in the horizontal direction and vertical direction; the processor may collect the information of the sensor and process the information, and deliver the processed data to the wireless transmitting module; the wireless transmitting module may correspond to the wireless receiving module in the 3D display position adjusting apparatus, and complete wireless data transmission and reception. A specific wireless transmission mode may be Bluetooth, infrared, WiFi, ZigBee, or the like.

In summary, the 3D display position adjusting method, apparatus and system provided by the exemplary embodiments of the present disclosure may adjust the position of the 3D display on the arcuate support so that when the viewing implementor of the 3D display changes a viewing angle, the 3D display can move along with the angle change, such that a better viewing effect is obtained.

Although the present disclosure has been described in detail above by taking a 3D display as an example, it should be understood that the described 3D display position adjusting method, apparatus and system are also applicable to non-3D displays.

It needs to be emphasized that in addition to terms specifically defined by the present disclosure, all technical and scientific terms used in the specification have the same meaning as commonly understood by those skilled in the art to which the present disclosure belongs.

It needs to be appreciated that the present disclosure uses expressions "an embodiment", "one embodiment" or "some embodiments" and their derivative expressions. These expression and terms mean that specific features, structures or properties described in conjunction with embodiments are included in at least one embodiment. The phrase "in an embodiment" at all occurrences of the present disclosure dos not necessarily refer to the same embodiment.

It should be appreciated that wording "a" and "an" in claims of the present disclosure do not exclude plurality, they are only intended for ease of description, and should not be understood as limiting the protection scope of the present disclosure.

Although the subject matter has been described in language specific to structural features and/or acts of methods, it should be understood that the subject matter defined in the appended claims is not limited to the specific features or acts described above. On the contrary, the specific features and acts described above are disclosed as exemplary forms of implementing the claims. It will be apparent to those skilled in the art that various modifications and variations can be made in the embodiments of the present disclosure without departing from the spirit and scope of the disclosure. Thus, if these modifications and variations of the present disclosure fall within the scope of claims of the present application and equivalent technologies thereof, the present disclosure intends to cover these modifications and variations.

The invention claimed is:

1. A display position adjusting apparatus, comprising:
a processor;
an arcuate bracket;
a height sensor; and
a support rod for supporting the arcuate bracket,
wherein the arcuate bracket comprises a first arcuate rod and a second arcuate rod perpendicular to each other,
wherein a display is on the second arcuate rod,
wherein the display is connected to the second arcuate rod through a first connector and configured to move along the second arcuate rod through the first connector under a control of the processor,
wherein the second arcuate rod is connected to the first arcuate rod through a second connector and configured to move along the first arcuate rod through the second connector under the control of the processor, wherein the height sensor is arranged on the arcuate bracket that is configured to measure a height of the arcuate bracket, and wherein the first arcuate rod is connected to the support rod through a third connector, and configured to move along the support rod through the third connector under the control of the processor according to height data of the height sensor.

2. The display position adjusting apparatus according to claim 1, wherein each of the first connector, the second connector and the third connector comprises a respective motor and a respective gear, wherein the respective motor is configured to drive the respective gear to rotate under the control of the processor, so that the first connector, the second connector and the third connector move along the second arcuate rod, the first arcuate rod and the support rod, respectively.

3. The display position adjusting apparatus according to claim 1, wherein the processor is configured to perform operations comprising:

obtaining angle change data of a viewing implementor of the display; and adjusting a position of the display on the arcuate bracket according to the angle change data of the viewing implementor of the display until a plane of the display is perpendicular to a line of sight of the viewing implementor of the display.

4. The display position adjusting apparatus according to claim 1, wherein radii of the first arcuate rod and second arcuate rod are equal in size.

5. The display position adjusting apparatus according to claim 1, wherein the display comprises a 3D display.

6. The display position adjusting apparatus according to claim 1, wherein the first connector and the second connector are two independent connectors that are not directly connected to each other.

7. A display position adjusting method using the display position adjusting apparatus according to claim 1, the display position adjusting method comprising:

obtaining angle change data of a viewing implementor of the display from the processor; and adjusting a position of the display on the arcuate bracket according to the angle change data of the viewing implementor of the display until a plane of the display is perpendicular to a line of sight of the viewing implementor of the display.

8. The method according to claim 7, wherein the angle change data comprises a vertical angle change value and a horizontal angle change value, wherein the first arcuate rod is vertically disposed, and the second arcuate rod is horizontally disposed, and wherein the adjusting the position of the display on the arcuate bracket comprises moving the second arcuate rod on the first arcuate rod by a first arc length corresponding to the vertical angle change value, and moving the display on the second arcuate rod by a second arc length corresponding to the horizontal angle change value.

9. The method according to claim 7, wherein the angle change data comprises a vertical angle change value and a horizontal angle change value, wherein the first arcuate rod is horizontally disposed, and the second arcuate rod is vertically disposed, wherein the adjusting the position of the display on the arcuate bracket comprises moving the display on the second arcuate rod by a first arc length corresponding to the vertical angle change value, and moving the second arcuate rod on the first arcuate rod by a second arc length corresponding to the horizontal angle change value.

10. The method according to claim 7, wherein before obtaining the angle change data of the viewing implementor of the display, the method further comprises:

adjusting the position of the arcuate bracket according to a position of the viewing implementor of the display such that an observation point of the viewing implementor of the display is at a sphere center of the arcuate bracket.

11. The method according to claim 10, wherein the adjusting the position of the arcuate bracket according to the position of the viewing implementor comprises:

adjusting a first height of the arcuate bracket to be consistent with a second height of the observation point of the viewing implementor of the display according to first height data of the observation point of the viewing implementor of the display and second height data determined by a height sensor on the arcuate bracket; and according to distance data of the viewing implementor of the display and the arcuate bracket, adjusting a distance between the arcuate bracket and the viewing implementor of the display to be consistent with a radius of the arcuate bracket.

12. The method according to claim 11, wherein the arcuate bracket is on a support rod, wherein the support rod is on a base, wherein the adjusting the first height of the arcuate bracket to be consistent with the second height of the observation point of the viewing implementor of the display comprises adjusting the position of the arcuate bracket on the support rod until the first height of the arcuate bracket is consistent with second height of the observation point of the viewing implementor of the display, and wherein the adjusting the distance between the arcuate bracket and the viewing implementor of the display to be consistent with the radius of the arcuate bracket comprises moving the base until the distance between the arcuate bracket and the viewing implementor of the display is consistent with the radius of the arcuate bracket.

13. A 3D display position adjusting system, comprising:

a 3D viewing device configured to transmit angle change data when a viewing angle of the 3D viewing device changes; and a 3D display position adjusting apparatus comprising a processor, an arcuate bracket, a height sensor and a support rod for supporting the arcuate bracket, wherein the arcuate bracket comprises a first arcuate rod and a second arcuate rod perpendicular to each other, wherein the 3D display is on the second arcuate rod, wherein the 3D display is connected to the second arcuate rod through a first connector and configured to move along the second arcuate rod through the first connector under a control of the processor, wherein the second arcuate rod is connected to the first arcuate rod through a second connector and configured to move along the first arcuate rod through the second connector under the control of the processor, and wherein the 3D display position adjusting apparatus is configured to obtain the angle change data of the 3D viewing device and adjust a position of the 3D display on the arcuate bracket according to the angle change data of the 3D viewing device until a plane of the 3D display is perpendicular to a line of sight of a user of the 3D viewing device, wherein the height sensor is arranged on the arcuate bracket that is configured to measure a height of the arcuate bracket, and wherein the first arcuate rod is connected to the support rod through a third connector, and configured to move along the support rod through the third connector under the control of the processor according to height data of the height sensor.

14. The system according to claim 13, wherein the angle change data comprises a vertical angle change value and a horizontal angle change value, wherein the first arcuate rod is vertically disposed, and the second arcuate rod is horizontally disposed, and wherein the 3D display position adjusting apparatus is configured to move the second arcuate rod on the first arcuate rod by a first arc length corresponding to the vertical angle change value, and move the 3D display on the second arcuate rod by a second arc length corresponding to the horizontal angle change value.

15. The system according to claim 13, wherein the angle change data comprises a vertical angle change value and a horizontal angle change value, wherein the first arcuate rod is horizontally disposed, and the second arcuate rod is vertically disposed, wherein the 3D display position adjusting apparatus is configured to move the 3D display on the second arcuate rod by a first arc length corresponding to the vertical angle change value, and move the second arcuate rod on the first arcuate rod by a second arc length corresponding to the horizontal angle change value.

16. The system according to claim 13, wherein the 3D display position adjusting apparatus is further configured to perform operations comprising:

before obtaining the angle change data of the 3D viewing device, adjusting a position of the arcuate bracket according to a position of the user so that the 3D viewing device is at a sphere center of the arcuate bracket.

17. The system according to claim 16, wherein the 3D viewing device is configured to obtain first height data of the 3D viewing device and distance data of the 3D viewing device and the arcuate bracket, and transmit the height data and the distance data to the 3D display position adjusting apparatus, and wherein the 3D display position adjusting apparatus is configured to perform operations comprising:

adjusting a first height of the arcuate bracket to be consistent with a second height of the 3D viewing device according to the first height data of the 3D viewing device and second height data determined by a height sensor on the arcuate bracket; and according to the distance data of the 3D viewing device and the arcuate bracket, adjust a distance between the arcuate bracket and the 3D viewing device to be consistent with a radius of the arcuate bracket.

18. The system according to claim 17, wherein the arcuate bracket is on a support rod, and wherein the support rod is on a base, wherein the 3D display position adjusting apparatus is configured to perform operations comprising:

adjusting the position of the arcuate bracket on the support rod until the first height of the arcuate bracket is consistent with the second height of the 3D viewing device, and moving the base until the distance between the arcuate bracket and the 3D viewing device is consistent with the radius of the arcuate bracket.

19. The system according to claim 13, wherein the first connector and the second connector are two independent connectors that are not directly connected to each other.

* * * * *